US007595059B2

(12) United States Patent
Tsang et al.

(10) Patent No.: US 7,595,059 B2
(45) Date of Patent: Sep. 29, 2009

(54) **METHODS AND COMPOSITIONS FOR DETECTING LARVAL *TAENIA SOLIUM* WITH A CLONED DIAGNOSTIC ANTIGEN**

(75) Inventors: Victor C. W. Tsang, Decatur, GA (US); Ryan M. Greene, San Antonio, TX (US); Patricia P. Wilkins, Gainesville, GA (US); Kathy Hancock, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 466 days.

(21) Appl. No.: 11/508,046

(22) Filed: Aug. 21, 2006

(65) Prior Publication Data

US 2007/0122853 A1 May 31, 2007

Related U.S. Application Data

(62) Division of application No. 10/240,982, filed as application No. PCT/US01/10392 on Mar. 30, 2001, now Pat. No. 7,094,576.

(60) Provisional application No. 60/194,418, filed on Apr. 4, 2000.

(51) Int. Cl.
*A61K 39/002* (2006.01)
*C12N 15/09* (2006.01)
*C12P 21/04* (2006.01)
*C07H 21/04* (2006.01)

(52) U.S. Cl. ............... 424/265.1; 424/190.1; 435/69.1; 435/69.3; 435/69.7; 536/23.1; 536/23.7

(58) Field of Classification Search .................. None
See application file for complete search history.

(56) References Cited

U.S. PATENT DOCUMENTS 5,354,660 A * 10/1994 Tsang et al. ............... 435/7.22

FOREIGN PATENT DOCUMENTS

WO   WO 01/10897   2/2001

OTHER PUBLICATIONS

Houghten et al. (Vaccines, 1986, Edited by Fred Brown: Cold Spring Harbor Laboratory).*
Holmes, Exp. Opin.Invest. Drugs, 2001, 10(3):511-519.*
Greenspan et al (Nature Biotechnology, 1999, 7:936-937).*
Burgess et al., "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue," *J. Cell Biol.* 111:2129-2138 (1990).
Chung et al., "A Recombinant 1-kDa Protein of *Taenia solium* Metacestodes Specific to Active Neurocysticercosis," *J. Infect. Dis.* 180:1307-1315 (1999).
De Aluja et al., "Experimental *Taenia solium* Cysticercosis in Pigs: Characteristics of the Infection and Antibody Responsse," *Vet. Parasitol.* 61:49-59 (1996).
Espinoza et al., Characterization by Enzyme-Linked Immunosorbent Assay of the Humoral Immune Response in Patients with Neurocysticercosis and Its Application in Immunodiagnosis, *J. Clin. Microbiol.* 24:536-541 (1986).
Greene et al., "*Taenia solium*: Molecular Cloning and Serologic Evaluation of 14- and 18-kDa Related, Diagnoostic Antigens," *J. Parasitol.* 86:1001-1007 (2000).
Ito, "Novel Antigens for Neurocysticercosis: Simple Method For Preparation and Evaluation for Serodiagnosis," *Am. J. Trop. Med. Hyg.* 59:291-294 (1998).
Jobling et al., "Analysis of Structure and Function of the B Subunit of Cholera Toxin by the Use of Site-directed Mutagenesis," *Mol. Microbiol.* 5:1755-1767 (1991).
Lazar et al., "Transforming Growth Factor α: Mutation of Aspartic Acid 47 and Leucine 48 Results in Different Biological Activities," *Mol. Cell. Biol.* 8:1247-1252 (1988).
Lederman et al., "A Single Amino Acid Substitution in a Common African Allele of the CD4 Molecule Ablates Binding of the Monoclonal Antibody, OKT4." *Mol. Immunol.* 28:1171-1181 (1991).
Lightowlers, "Eradication of *Taenia solium* cysticercosis: A Role for Vaccination of Pigs," *Intl. J. Parasitol.* 29:811-817 (1999).
McManus, "Improved Diagnosis as an Aid to Better Surveillance of *Taenia solium* Cysticercosis, a Potential Public Health Threat to Papua New Guinea," *PNG Med. J.* 38:287-294 (1995).
Rudinger et al., in "Peptide Hormones," edited by Parsons, J.A., University Park Press, Jun. 1976, pp. 1-5.
Tsang et al., "An Enzyme-Linked Immunoelectrotransfer Blot Assay and Glycoprotein Antigens for Diagnosing Human Cysticercosis (*Taenia solium*)," *J. Infect. Dis.* 159:50-59 (1989).
Tsang et al., "Efficacy of the Immunoblot Assay for Cysticercosis in Pigs and Modulated Expression of Distinct IgM/IgG Activities to *Taenia solium* Antigens in Experimental Infections," *Vet. Immunol. Immunopathol.* 29:69-78 (1991).

\* cited by examiner

*Primary Examiner*—Robert B Mondesi
*Assistant Examiner*—Padma V Baskar
(74) *Attorney, Agent, or Firm*—Klarquist Sparkman, LLP

(57) ABSTRACT

Compositions and methods for the detection of *Taenia solium* and the diagnosis of *T. solium* infection are described. The nucleotide and amino acid sequences of the antigenic *T. solium* polypeptides gp50a, gp50b and gp50c are provided. The compositions contain synthetic antigenic polypeptides of larval origin prepared using the sequences described herein. Probes and primers for the detection or amplification of *T. solium* nucleic acid molecules are also described. The polypeptides can be administered to a human or animal to protect against *T. solium* infection. In addition, the polypeptides are useful as research tools for studying *T. solium* and as reagents in assays for the detection of *T. solium* antibodies in a biological sample. The methods are sensitive and specific assays that utilize the stable recombinant or synthetic antigenic polypeptides or nucleic acid molecules encoding the larval polypeptides.

11 Claims, No Drawings

METHODS AND COMPOSITIONS FOR DETECTING LARVAL *TAENIA SOLIUM* WITH A CLONED DIAGNOSTIC ANTIGEN

This is a divisional of U.S. application Ser. No. 10/240,982, filed Feb. 20, 2003 now U.S. Pat. No. 7,094,576, which is a § 371 U.S. national stage of International application No. PCT/US01/10392, filed Mar. 30, 2001, which claims the benefit of U.S. Provisional Application 60/194,418, filed Apr. 4, 2000.

This invention was made by the Centers for Disease Control and Prevention, an agency of the United States Government. Therefore, the United States Government has certain rights in this invention.

FIELD

The present disclosure relates to the fields of molecular biology and immunology and more specifically relates to compositions and methods for diagnosing cysticercosis. In particular, the disclosure pertains to synthetic or recombinant *Taenia solium* antigens and their use in immunoassays for diagnosis of cysticercosis.

BACKGROUND

*Taenia solium* cysticercosis, caused by infection with *T. solium* larval cysts, occurs in both humans and swine, resulting in significant public health and economic hardship. *T. solium*, also referred to as the pork tapeworm, is a helminth that exists in both a mature tapeworm form and a larval form. The lifecycle of *T. solium* begins when swine, the intermediate hosts, ingest tapeworm eggs excreted in the feces of a tapeworm carrier. The larvae hatch from the eggs and invade most tissues of the swine, giving rise to the disease cysticercosis.

When humans ingest raw or undercooked meat from cysticercotic swine, tapeworms, or taeniasis, develop. Patients with taeniasis may exhibit epigastric discomfort, nausea, irritability, diarrhea, and weight loss. In addition, proglottids, or individual segments of the tapeworm that are self-contained hermaphroditic reproductive units, may obstruct the appendix, biliary duct, or pancreatic duct.

Humans may also ingest *T. solium* eggs present in contaminated food and water and become infected with the larval form. After *T. solium* eggs are ingested, cysticerci may develop in the subcutaneous tissues, muscles, heart, lungs, liver, brain, and eye. Although small numbers of viable cysticerci may fail to produce symptoms in the infected host, death of the larvae stimulate a marked inflammatory reaction, fever, muscle pains, and eosinophilia. If the larvae invade the central nervous system, a single cyst may cause disease. The host may develop meningoencephalitis, epileptic seizures, dementia and other neurologic or psychiatric manifestations, and death can result from acute intracranial hypertension. The various manifestations of neurologic dysfunction caused by *T. solium* infection are collectively termed neurocysticercosis. Although neurocysticercosis can include many neurological symptoms, epilepsy is the most common symptom. In fact, *T. solium* is considered the leading infectious cause of epileptic seizures worldwide. Additionally, *T. solium* neurocysticercosis has a current worldwide toll of 50 million cases with 50,000 deaths each year.

Neurocysticercosis is rarely acquired in the United States; however, the disease is common in Latin America, Asia, Russia, and Eastern Europe. In Mexico, the mean rate for cysticercotic pigs in inspected slaughterhouses during 1980-1981 was 1.55%, and in rural areas of Mexico and South America, where sewage disposal is limited, the proportion of cysticercotic pigs can be in excess of 50%. In these and other developing countries, the parasite causes a substantial economic burden to the pork industry. Additionally, due to the increased travel and immigration from highly endemic areas, detection and treatment of *T. solium* related diseases has become a U.S. public health priority.

Diagnosis historically relied on histological identification of the parasite by biopsy or autopsy. The recent development of radiologic and serologic methods has improved diagnosis. However, while radiologic methods such as computed tomography (CT) or nuclear magnetic resonance imaging are useful in diagnosing neurocysticercosis, they are often too expensive or inaccessible in developing countries.

Although some diagnostic tests are currently available to identify *T. solium* infection and diagnose neurocysticercosis, these tests lack specificity and sensitivity. A more specific and sensitive assay for diagnosing human neurocysticercosis by detecting the presence of *T. solium* larvae using immunoelectrotransfer blot (EITB) is described in U.S. Pat. No. 5,354,660 to Tsang et al. This test is the only test approved by the Pan American Health Organization. However, the assay utilizes purified, naturally-occurring *T. solium* larval glycoproteins, which makes the assay reagents expensive and difficult to produce.

In developing countries where *T. solium*-related diseases are endemic, access to diagnostic assays may be limited due to the high cost of using antigens that are produced using complicated purification procedures. Furthermore, because cysticercosis is most prevalent in rural areas of developing countries, a field test is needed for epidemiological studies and surveillance. A field assay using inexpensive and reliable reagents could be an important tool in breaking the transmission cycle of the parasite, enabling the on-site diagnosis of infected pigs and immediate treatment with anti-helminthic agents such as oxfendazole. A field diagnosis of cysticercosis would also serve as an economic benefit to pig farmers, because uninfected pigs command a higher price.

SUMMARY OF THE DISCLOSURE

This disclosure provides simple, sensitive methods for the diagnosis of cysticercosis and/or neurocysticercosis, and compositions for use in such methods.

Embodiments include a method for the detection of *T. solium* cysticercosis, particularly the diagnosis or monitoring of *T. solium* infection in humans and animals, which is inexpensive, sensitive, and accurate, with little or no cross-reactivity.

Also provided are stable reagents for the detection of *T. solium* in a biological sample wherein the reagents can be relatively inexpensively produced.

Other embodiments include nucleic acid and amino acid sequences for immunogenic *T. solium* larval glycoproteins. Molecules having these sequences can be used for the production of large quantities of highly pure polypeptide.

Yet another embodiment provides rapid, simple, and inexpensive assays for the detection of *T. solium* larvae. In specific examples, the assay has a long shelf life, a short assay time, and/or stable reagents that can be utilized in the field. In specific examples, the result produced from assays provided herein can be interpreted without the use of instrumentation or special temperature conditions.

In certain embodiments, methods are provided for detecting the presence of antibodies in a biological sample, wherein the antibodies are reactive with at least one *T. solium* larval antigen, which antigen has been produced recombinantly or synthetically. Such antibodies may also bind to naturally occurring *T. solium* larval antigens, for instance naturally occurring antigens that have been isolated by lentil lectin affinity chromatography.

Further embodiments include compositions that contain recombinant or synthetic *T. solium* larval peptides or polypeptides, which are useful in immunoassays for the detection of larval *T. solium* in biological samples. Such polypeptides may be recombinantly or synthetically produced using the provided nucleic acid or amino acid sequences.

Examples of provided recombinant or synthetic peptides or polypeptides (or fragments thereof) correspond naturally-occurring *T. solium* glycoproteins such as gp50, wherein gp indicates that the antigen is a glycoprotein and the number indicates the approximate molecular weight in kilodaltons (kDa) as determined by SDS-PAGE analysis. Certain provided polypeptides correspond to glycoproteins having a molecular weight of approximately 50 kDa, as determined by SDS-PAGE analysis; these recombinant or synthetic polypeptides are, therefore, referred to herein as gp50 polypeptides. Antigenic, immunogenic or immunodominant fragments of these gp50 polypeptides are also described.

In specific examples, the recombinant larval polypeptides and peptides are encoded by the nucleic acid sequences of SEQ ID NOs: 1, 3, or 5, and have the corresponding amino acid sequences of SEQ ID NOs: 2, 4, or 6, respectively. Recombinant or synthetic polypeptides having the foregoing nucleic acid or amino acid sequences, or antigenic fragments thereof, are useful in immunoassays for the detection of *T. solium*, and are herein referred to as gp50a, -b and -c, respectively.

Amino acid sequences provided herein are useful for the synthesis of the antigens or antigenic fragments using known chemical synthesis techniques.

Nucleic acid molecules encoding *T. solium* larval antigens are useful for the recombinant production of the antigens and antigen fragments, and are also useful as molecular probes or primers for the detection of ribonucleic acid (RNA) and deoxyribonucleic acid (DNA) involved in transcription and translation of *T. solium* peptides. Such molecular probes or primers provide highly specific and sensitive means to detect and measure *T. solium* larval polypeptides in tissues and cells.

Recombinant or synthetic *T. solium* polypeptides can be used in diagnostic kits to detect the presence and quantity of *T. solium* antibodies, which are diagnostic or prognostic for the occurrence, recurrence or treatment of diseases such as cysticercosis and neurocysticercosis. The recombinant or synthetic *T. solium* polypeptides may also be administered to a human or animal in a pharmaceutical composition to immunize the human or animal against *T. solium* infection, thereby reducing or preventing *T. solium* infection and/or related disease.

Methods provided herein include immunoassays directed toward the detection of *T. solium* antibodies in biological samples, such as biological fluids and tissues of humans and animals. Other provided methods are nucleic acid hybridization and amplification assays directed toward the detection of *T. solium* antigens in biological samples.

In one embodiment, an immunoassay employs one or more of the recombinant or synthetic larval polypeptides, or antigenic fragments thereof, described herein, with one or more other larval polypeptides of *T. solium* for the detection of anti-larval antibodies in a biological sample. An example of such an immunoassay is a rapid immunochromatographic diagnostic test (such as a card test) containing recombinant larval antigens, or antigenic fragments thereof, immunoreactive with anti-*T. solium* antibodies in a biological sample. In other examples, methods are immunoblot and ELISA tests.

Diagnostic and analytical methods and kits and provided for detection and measurement of *T. solium* antibodies in a variety of samples. Such kits can be in any configuration known to those of ordinary skill in the art.

These and other features and advantages of the present invention will become apparent after a review of the following detailed description of the disclosed embodiments and the appended claims.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the nucleic acid and encoded amino acid sequence of *T. solium* larval antigenic polypeptide gp50a.

SEQ ID NO: 2 shows the amino acid sequence of *T. solium* larval antigenic peptide gp50a.

SEQ ID NO: 3 shows the nucleic acid and encoded amino acid sequence of *T. solium* larval antigenic polypeptide gp50b.

SEQ ID NO: 4 shows the amino acid sequence of *T. solium* larval antigenic peptide gp50b.

SEQ ID NO: 5 shows the nucleic acid and encoded amino acid sequence of *T. solium* larval antigenic polypeptide gp50c.

SEQ ID NO: 6 shows the amino acid sequence of *T. solium* larval antigenic peptide gp50c.

DETAILED DESCRIPTION

Compositions and methods for detecting *T. solium* infection and diagnosing diseases related to *T. solium* infection are provided. The compositions comprise one or more recombinant or synthetic immunogenic, or immunodominant, polypeptides or peptides (or fragments thereof) of the *T. solium* helminth larvae, for instance the polypeptides referred to herein as gp50a, -b, -c or antigenic fragments thereof. The nucleic acid sequences and amino acid sequences of several cDNA clones of *T. solium* larvae polypeptides are provided.

Recombinant *T. solium* polypeptides are useful as diagnostic reagents in the immunoassays described below. The polypeptides are also useful in vitro as research tools for studying *T. solium* in general and *T. solium* diseases such as cysticercosis. Additionally, the polypeptides are useful in pharmaceutical compositions such as vaccines to elicit an immune response in a subject.

Methods provided herein include assays for the detection or quantitation of anti-*T. solium* antibodies or *T. solium* nucleic acid molecules in a sample such as a human or animal fluid or tissue. One or more recombinant or synthetic *T. solium* polypeptides, or antigenic fragments thereof, or nucleic acid molecules encoding the *T. solium* polypeptides, or probes and primers thereof, are used as reagents in the assays.

Also provided are methods for eliciting an immune response in a subject, wherein the immune response is to a *T. solium* polypeptide (e.g., a gp50 polypeptide). In examples of such methods, a composition comprising one or more polypeptide, or one or more antigenic fragments of such polypeptides, is introduced into the subject (e.g., by injection). In other examples, a nucleic acid molecule encoding such a polypeptide or antigenic fragment is introduced into the subject. In specific embodiments, the elicitation of an immune response in the subject will lead to partial, or in some instances complete, resistance in that subject to infection by *T. solium*.

Terms

Unless otherwise noted, technical terms are used according to conventional usage. Definitions of common terms in molecular biology may be found in Benjamin Lewin, *Genes VII*, published by Oxford University Press, 2000 (ISBN 0-19-899276-X); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments, the following explanation of terms is provided:

The terms "a," "an," and "the" as used herein mean "one or more" and include the plural unless the context is inappropriate.

The term "antibodies" as used herein includes monoclonal antibodies, polyclonal chimeric, single chain, bispecific, simianized, and humanized antibodies as well as Fab fragments, including the products of an Fab immunoglobulin expression library.

The term "antigen" refers to a molecule, or fragment thereof, which can induce an immune response in a mammal. The term includes immunogens and regions responsible for antigenicity or antigenic determinants. "Antigenic determinant" refers to a region of a *T. solium* protein recognized by an antibody.

The "condition" or "conditions" under which a DNA strand is synthesized include the presence of nucleotides, cations, and appropriate buffering agents in amounts and at temperatures such that the nucleic acid molecule and a DNA primer will anneal and oligonucleotides will be incorporated into a synthesized DNA strand.

As used herein, the terms "detecting" or "detection" refers to quantitatively or quantitatively determining the presence of a biomolecule under investigation.

By "isolated" is meant a biological molecule substantially free from at least some of the components with which it naturally occurs. Nucleic acids and proteins that have been "isolated" include nucleic acids and proteins purified by standard purification methods. The term also embraces nucleic acids and proteins prepared by recombinant expression in a host cell as well as chemically synthesized nucleic acids. As with the term purified, isolated is a relative term.

The terms "polypeptide", "peptide", and "protein", as used herein, are interchangeable and mean a biomolecule composed of two or more amino acids linked by a peptide bond. The term "polypeptide" includes smaller (e.g., antigenic) fragments of the larger biomolecules.

The term "synthetic polypeptide" refers to a polypeptide formed, in vitro, by joining amino acids in a particular order, using the tools of organic chemistry to form the peptide bonds.

As used herein, the term "primer" or "DNA primer" means an oligonucleotide that anneals to a nucleic acid molecule in a particular orientation to allow for the synthesis of a nascent DNA strand in the presence of a polymerase under the conditions described herein.

As used herein, the term "primer pair" refers to two primers, one having a forward designation and the other having a reverse designation (relative to their respective orientations on a double-stranded DNA molecule that consists of a sense and antisense sequence), such that under amplification conditions (such as those described herein) the forward primer anneals to and primes amplification of the sense sequence and the reverse primer anneals to and primes amplification of the antisense sequence. Primers can be selected for use in the amplification reaction on the basis of having minimal complementarity with other primers in the reaction (to minimize the formation of primer dimers) and having $T_m$ values with a range of reaction temperatures appropriate for the amplification method, such as PCR. In addition, primers can be selected to anneal with specific regions of the DNA or RNA template such that the resulting DNA amplification product ranges in size from 100 to 5000 base pairs in length, for instance around 300 base pairs in length or longer.

By "probe" is meant a nucleic acid sequence that can be used for selective hybridization with complementary nucleic acid sequences for their detection. The probe can vary in length from about 5 to 100 nucleotides, or from about 10 to 50 nucleotides, or about 18 to 24 nucleotides. The terms "probe" or "probes" as used herein are defined to include "primers."

The term "purified" as it is used herein does not require absolute purity; rather, it is intended as a relative term. Thus, for example, a purified nucleic acid preparation is one in which the specified protein is more enriched than the nucleic acid is in its generative environment, for instance within a cell or in a biochemical reaction chamber. A preparation of substantially pure nucleic acid may be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation.

As used herein, the term "recombinant" refers to a form of a synthetic peptide made using technology well known in the art of molecular biology.

Unless otherwise explained, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and are not intended to be limiting. All of the patents, publications, and other references mentioned herein are hereby incorporated by reference.

*Taenia solium* Polypeptides and Polypeptide Fragments

Certain compositions provided herein contain recombinant or synthetic *T. solium* larval polypeptides that are immunoreactive with *T. solium* antibodies. *T. solium* antibodies are, in certain embodiments, derived from the sera, saliva, cerebrospinal fluid or urine of patients infected with *T. solium*. In specific examples, the antibodies are *T. solium* patient sera antibodies. Alternatively, the antibodies are monoclonal antibodies.

In specific embodiments, the recombinant or synthetic polypeptides correspond to naturally occurring glycoproteins having molecular weights of approximately 50 kDa. Examples of such polypeptides, referred to herein as gp50a, -b and -c, contain the amino acid sequences provided in the attached Sequence Listing as SEQ ID NOs: 2, 4 and 6, respectively. In certain instances, these polypeptides are encoded by the nucleic acid sequences set forth in SEQ ID NOs: 1, 3 and 5, respectively, but this is not necessary (e.g., through the redundancy of the genetic code).

The disclosed immunoreactive polypeptides include polypeptide analogs, which are antigenic peptides containing amino acid sequences differing from those shown in SEQ ID NOs: 2, 4, or 6 by one or more amino acid substitutions at any position or which have other molecules attached to amino acid functional groups within the sequence. Also disclosed are immunoreactive fragments (antigenic fragments) of the specifically provided polypeptides, which fragments have substantially the same antigenicity of the related polypeptide, or the functional equivalent thereof. In certain embodiments, these antigenic fragments contain amino acid sequences that are homologous or substantially homologous to one, two or all three of the antigenic polypeptides (gp50a, -b, and -c). In specific examples of these embodiments, the antigenic fragments contain amino acid sequences that are homologous or substantial homologous to the three gp50 clones.

*T. solium* polypeptides described herein have a variety of uses. For example the polypeptides or polypeptide fragments (e.g., antigenic fragments) are used as reagents in immunoassays for the detection of *T. solium* antibodies as described in more detail below. Furthermore, *T. solium* polypeptides may be employed to develop affinity columns for isolating *T. solium* antibodies. Also, polypeptides that bind to *T. solium* antibodies with high specificity and avidity may be labeled with a label or reporter group and employed for visualization and quantitation in the assays described herein using detection techniques such as autoradiographic and membrane binding techniques. The reporter group or label is commonly a fluorescent or radioactive group or an enzyme. Such applications provide important diagnostic and research tools.

Nucleic Acid Molecules

Nucleic acid molecules encoding the *T. solium* larval polypeptides described above, and probes or primers that hybridize to nucleic acid molecules encoding such polypeptides, are provided. The nucleic acid molecules include those having sequences encoding the larval *T. solium* polypeptide gp50 clones gp50a, gp50b, and gp50c, or fragments thereof. Sequences for the three specific clones are provided in the attached Sequence Listing as SEQ ID NOs: 1, 3, and 5, respectively.

Nucleic acid molecules are useful for production of recombinant polypeptides. Because recombinant methods of polypeptide production produce large quantities of polypeptide that require less purification, recombinant polypeptides are often less expensively produced than polypeptides produced using traditional isolation or purification techniques. One or more of the nucleic acid sequences encoding the *T. solium* peptides can be inserted into a vector, such as a plasmid, and recombinantly expressed in a living organism to produce recombinant *T. solium* peptides in accordance with methods well known to those of ordinary skill in the art, for instance using methods as described in more detail below.

Nucleic acid molecules (and fragments or portions thereof) are also useful as nucleic acid probes or primers for the detection of *T. solium* infection in a biological specimen, with high sensitivity and/or specificity. The probes or primers can be used to amplify or detect *T. solium* larvae nucleic acid molecules in the sample, quantify the amount of *T. solium* in the sample, diagnose infection or determine contamination with *T. solium*, or monitor the progress of therapies used to treat the infection. The nucleic acid molecules described herein are also useful as laboratory research tools to study the *T. solium* organism and diseases associated with this organism (such as cystercercosis and neurocystercercosis) and to develop therapies and treatments for such diseases.

Detectable probes are labeled with a detectable label as described herein with respect to labeled polypeptides.

Nucleic acid probes or primers provided herein selectively hybridize with nucleic acid molecules encoding *T. solium* larval (poly) peptides described herein, or sequences complementary thereto. Hybridization may be achieved under various temperature and conditions, according to the temperature of dissociation ($T_d$) of the molecules being hybridized and the stringency required for specific binding. The molecules can be hybridized to one another in any order or at the same or essentially the same time. Reaction conditions for hybridization of an oligonucleotide, or polynucleotide, to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. Under extremely stringent hybridization conditions, only oligomers that are completely complementary to each other will remain hybridized to each other. In general, the longer the sequence, or higher the G and C content, the higher the temperature required or salt concentration permitted. Chapter 11 of Sambrook et al. (MOLECULAR CLONING: A LABORATORY MANUAL, 2nd ed., Cold Spring Harbor Laboratory Press, Cold Spring Harbor, N.Y., 1989), describes hybridization conditions for oligonucleotide probes and primers in great detail, including a description of the factors involved and the level of stringency necessary to guarantee hybridization with a desired specificity.

If used as primers, nucleic acid molecule compositions described in certain embodiments will include at least two nucleic acid molecules that hybridize to different regions of the target molecule so as to amplify a desired region of that target. Depending on the length of the probe or primer, the target region can range between 70% complementary bases and full complementarity and still hybridize under stringent conditions. In specific embodiments, the hybridizing nucleic acid probes or primers described herein have at least 70%, 80%, 85%, 90%, 95%, 97%, 98%, or at least 99% complementarity with the segment of the sequence to which they hybridize, for instance 85% or more. For the purpose of determining the presence of *T. solium*, the degree of complementarity between the hybridizing nucleic acid (probe or primer) and the sequence to which it hybridizes is at least enough to distinguish hybridization with a nucleic acid from other organisms.

In particular embodiments, each probe or primer is a DNA molecule having a length of 20 to 40 nucleotides. In some embodiments, the length of the primer is 25 to 35 nucleotides, or for instance 27 to 29 nucleotides.

The amplification of the synthesized DNA can be detected by any method for the detection of DNA known in the art. Such detection include by Southern blot hybridization assay, by visualization of DNA amplification products of specific molecular weight on ethidium bromide stained agarose gels, by measurement of the incorporation of radiolabeled nucleotides into the synthesized DNA strand by autoradiography or scintillation measurement, by ELISA modified for the capture of a detectable moiety bound to the amplified DNA, or any other detection method known to one of ordinary skill in the art. One particular detection method is by hybridization of the amplified DNA to an internal specific oligo-probe using techniques such as ELISA, Southern blot hybridization or similar methods.

Also provided herein are sequences, probes and primers that selectively hybridize to the encoding nucleic acid or the complementary, or opposite (or antisense), strand of nucleic acid as those specifically provided herein. Specific hybridization with a nucleic acid can occur with minor modifications or substitutions in the nucleic acid, so long as functional, species-specific hybridization capability is maintained. Isolated nucleic acids are provided herein that selectively hybridize with the nucleic acids encoding the *T. solium* larval polypeptides under stringent conditions, and which have at least five nucleotides complementary to the sequence of interest, as described by Sambrook et al. (MOLECULAR CLONING: A LABORATORY MANUAL, 2nd ed. Cold Spring Harbor Laboratory Press, Cold Spring Harbor, N.Y., 1989).

It will be understood by those ordinarily skilled in the art that the *T. solium* polypeptides described herein are also encoded by sequences substantially similar to the nucleic acid sequences provided in the Sequence Listing. By the phrase "substantially similar" is meant a nucleic acid (including DNA and RNA) sequence which, by virtue of the degeneracy of the genetic code, is not identical with that shown in any of SEQ ID NOs: 1, 3 or 5, but which still encodes the same amino acid sequence; or a nucleic acid sequence which encodes a different amino acid sequence but retains the activities or antigenicity of the specific polypeptide, either because one amino acid is replaced with another similar amino acid, or because the change (whether it be substitution, deletion or insertion) does not affect the active site of the protein.

Production of Synthetic or *T. solium* Larvae Polypeptides

The nucleic acid sequences provided herein are useful for the production of the proteins, polypeptides or peptides that they encode, or antigenic fragments thereof, by either recombinant or synthetic methods known to those skilled in the art. For example, one or more of the nucleotide sequences provided herein, or a homologue or functional equivalent or portion thereof, can be inserted into a vector, such as a plasmid, and recombinantly expressed in a living organism to produce recombinant polypeptides. Alternatively, peptides can be synthesized by solid phase techniques, cleaved from the resin, and purified by preparative high performance liquid chromatography (e.g., see Creighton, 1983, PROTEINS STRUCTURES AND MOLECULAR PRINCIPLES, W. H. Freeman and Co., N.Y. pp. 50-60). The composition of the synthetic peptides may be confirmed by amino acid analysis or sequence analysis) (e.g., the Edman degradation procedure; see Creighton, 1983, PROTEINS, STRUCTURES AND MOLECULAR PRINCIPLE, W. H. Freeman and Co., N.Y., pp. 34-49). Also smaller peptides can be joined together to form larger polypeptides by a method known as chemical ligation (Wilken and Kent, *Current Opinion in Biotechnology* 4: 412-426, 1998).

Recombinant proteins are produced by methods well known to those skilled in the art. A cloning vector, such as a plasmid or phage DNA is cleaved with a restriction enzyme and the nucleic acid sequence encoding the proteins or fragments thereof of interest is inserted into the cleavage site and ligated. The cloning vector is then inserted into a host to produce the protein or fragment encoded by the nucleic acid. Suitable hosts include bacterial hosts such as *Escherichia coli, Bacillus subtilis*, yeasts, plants, insects and mammalian cell lines, and other cell cultures. Insect cell expression may be a beneficial host for generating a large amount of protein for use in a diagnostic assay. Yeasts are beneficial hosts for vaccine or pharmaceutical product expression. Production and purification of the gene product may be achieved and enhanced using known molecular biology techniques. Combining various nucleic acid sequences in a cloning vector may also produce mosaic peptides.

Examples of appropriate cloning and sequencing techniques, and instructions sufficient to direct per s of skill through many cloning exercises are found in Berger and Kimmel, GUIDE TO MOLECULAR CLONING TECHNIQUES, METHODS IN ENZYMOLOGY volume 152 Academic Press, Inc., San Diego, Calif.; Sambrook et al. (1989) MOLECULAR CLONING—A LABORATORY MANUAL (2nd ed.) Vol. 1-3, Cold Spring Harbor Laboratory Press, Cold Spring Harbor, N.Y.; and CURRENT PROTOCOLS IN MOLECULAR BIOLOGY, F. M. Ausubel et al., eds., Current Protocols, a joint venture between Greene Publishing Associates, Inc. and John Wiley & Sons, Inc., (1994 Supplement). Product information from manufacturers of biological reagents and experimental equipment also provide information useful in known biological methods. Such manufacturers include the SIGMA Chemical Company (Saint Louis, Mo.), R&D Systems (Minneapolis, Minn.), Amersham Pharmacia Biotech (Piscataway, N.J.), CLONTECH Laboratories, Inc. (Palo Alto, Calif.), ChemGenes Corp. (Ashland, Mass.), Aldrich Chemical Company (Milwaukee, Wisc.), Glen Research, Inc. (Sterling, Va.), Life Technologies, Inc. (Rockville, Md.), Fluka Chemica-Biochemika Analytika (Buchs, Switzerland), Invitrogen (Carlsbad, Calif.), and Perkin-Elmer Corp., Applied Biosystems Division (Foster City, Calif.), as well as many other commercial sources known to one of skill.

Provided with the peptide sequences described herein, one of skill will recognize a variety of equivalent nucleic acids that encode the peptides. This is because the genetic code requires that each amino acid residue in a peptide is specified by at least one triplet of nucleotides in a nucleic acid which encodes the peptide. Due to the degeneracy of the genetic code, many amino acids are equivalently coded by more than one triplet of nucleotides. For instance, the triplets CGU, CGC, CGA, CGG, AGA, and AGG all encode the amino acid arginine. Thus, at every position where an arginine is to be encoded by a nucleic acid triple, the nucleic acid may have any of the triplets that encode arginine. One of skill is thoroughly familiar with the genetic code and its use. An introduction to the subject is found in, for example, chapter 15 of Watson, et al., MOLECULAR BIOLOGY OF THE GENE (4$^{th}$ Ed., The Benjamin/Cummings Company, Inc., Menlo Park, Calif., 1987), and references cited therein.

Although any nucleic acid triplet or codon that encodes an amino acid can be used to specify the position of the amino acid in a peptide, certain codons are preferred by certain organisms. In some embodiments, it is desirable to select codons for elevated expression of an encoded peptide, for example, when the peptide is purified for use as an immunogenic reagent. Codons may be selected by reference to species codon bias tables, which tables show which codons are most typically used by the organism in which the peptide is to be expressed. The codons used frequently by an organism are translated by the more abundant t-RNAs in the cells of the organism. Because the t-RNAs are abundant, translation of the nucleic acid into a peptide by the cellular translation machinery is facilitated. Codon bias tables are available for most organisms. For an introduction to codon bias tables, see, e.g., Watson, et al., supra.

In addition, it will be readily apparent to those of ordinary skill in the art that the peptides described herein, and the nucleic acid molecules encoding such immunogenic peptides, can be subject to various changes, such as insertions, deletions, and substitutions, either conservative or non-conservative, where such changes might provide for certain advantages in their use, i.e., to increase biological activity.

One of ordinary skill will appreciate that many conservative variations of nucleic acid constructs yield a functionally identical construct. For example, due to the degeneracy of the genetic code, silent substitutions (i.e., substitutions of a nucleic acid sequence which do not result in an alteration in an encoded peptide) are an implied feature of every nucleic acid sequence which encodes an amino acid. In addition, one of skill will recognize many ways of generating alterations in a given nucleic acid construct. Such well-known methods include sites-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) Gene 8:81-97, Roberts et al. (1987) Nature 328:731-734 and Sambrook, Ausbel, Berger and Kimmel, all supra.

Modifications to nucleic acids are evaluated by routine screening techniques in suitable assays for the desired characteristic. For instance, changes in the immunological character of encoded peptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Similarly, conservative amino acid substitutions, in one or a few amino acids in an amino acid sequence of a protein are substituted with different amino acids with highly similar properties (see, the definitions section, supra), are also readily identified as being highly similar to a disclosed construct. By conservative substitutions is meant replacing an amino acid residue with another that is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are a feature of the present disclosure.

Various techniques for preparing synthetic polypeptides can be used. Solid phase synthesis in which the C-terminal amino acid of the peptide sequence is attached to an insoluble support followed by sequential addition of the remaining amino acids in the sequence is a useful and well known method for preparing the synthetic peptides. Techniques for solid phase synthesis are described by Barany and Merrifield, *Solid-Phase Peptide Synthesis*, in *The Peptides: Analysis, Synthesis, Biology* (Gross and Meienhofer (eds.), Academic Press N.Y., vol. 2, pp. 3-284 (1980)); Merrifield, et al., *J. Am. Chem. Soc.* 85, 2149-2156 (1963); and Stewart, et al., *Solid Phase Peptide Synthesis* (2nd ed., Pierce Chem. Co., Rockford, Ill. (1984)), the teachings of which are hereby incorporated by reference. Many automated systems for performing solid phase peptide synthesis are commercially available.

Solid phase synthesis is started from the carboxy-terminal end (i.e., the C-terminus) of the peptide by coupling a protected amino acid via its carboxyl group to a suitable solid support. The solid support used is not a critical feature provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those of skill in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resin, and the like. Such resins are commercially available and their methods of preparation are known to those of ordinary skill in the art.

The acid form of the peptides may be prepared by the solid phase peptide synthesis procedure using a benzyl ester resin as a solid support. The corresponding amides may be produced by using benzhydrylamine or methylbenz-hydrylamine resin as the solid support. Those skilled in the art will recognize that when the BHA or MBHA resin is used, treatment with anhydrous hydrofluoric acid to cleave the peptide from the solid support produces a peptide having a terminal amide group.

The α-amino group of each amino acid used in the synthesis should be protected during the coupling reaction to prevent side reactions involving the reactive α-amino function. Certain amino acids also contain reactive side-chain functional groups (e.g., sulfhydryl, amino, carboxyl, hydroxyl, etc.) which must also be protected with appropriate protecting groups to prevent chemical reactions from occurring at those sites during the peptide synthesis. Protecting groups are well known to those of skill in the art.

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the α-amino protecting group, and must be removable after completion of the peptide synthesis under conditions that will not alter the structure of the peptide.

Coupling of the amino acids may be accomplished by a variety of techniques known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodiimide (DCC) or N,N-'diisopropylcarbodiimide (DIPCDI). Frequently, hydroxybenzotriazole (HOBt) is employed as a catalyst in these coupling reactions. Appropriate synthesis chemistries are disclosed in THE PEPTIDES: ANALYSIS, STRUCTURE, BIOLOGY, VOL. 1: METHODS OF PEPTIDE BOND FORMATION (Gross and Meienhofer (eds.), Academic Press, N.Y. (1979)); and Izumiya, et al., SYNTHESIS OF PEPTIDES (Maruzen Publishing Co., Ltd., (1975)).

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl)phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Novartis (Switzerland) or Bachem (California)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art. It should be noted that because the immunogenic peptides are relative short in length, this later approach (i.e., the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride ($CH_2Cl_2$), or mixtures thereof. If coupling is incomplete, the coupling reaction may be repeated before deprotection of the N-amino group and addition of the next amino acid. Coupling efficiency may be monitored by a number of means well known to those of skill in the art. A specific method of monitoring coupling efficiency is by the ninhydrin reaction. Peptide synthesis reactions may be performed automatically using a number of commercially available peptide synthesizers (e.g., Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, in particularly embodiments about 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides can be isolated and purified from the reaction mixture by means of peptide purification well known to those of skilled in the art. For example, the peptides may be purified using known chromatographic procedures such as reverse phase HPLC, gel permeation, ion exchange, size exclusion, affinity, partition, or countercurrent distribution.

Making or Identifying Antigenic Fragments

To identify antigenic fragments, synthetic or recombinant peptides or polypeptides can be generated by any of the procedures described above. The peptides can be absorbed to a plastic microwell, nitrocellulose, other membranes, or any other appropriate support. A peptide may be cross-linked to itself using a cross-linking agent, such as glutaraldehyde or cross-linked to a carrier protein, such as albumin, keyhole-limpet hemocyanin prior to absorption to the support. Antibodies present in body fluids from patients with cysticercosis or monoclonal antibodies specific for *T. solium* antigens bind the antigenic peptides or polypeptides and are detected using any immunoassay described below. Reactivity with the antibodies identifies an antigenic fragment.

Smaller peptides can be linked together to form polypeptides ranging in size from 40 aa to 200 aa by a method known as chemical ligation. (Wilken and Kent, 1998).

Labeled Polypeptides

When labeled with a detectable biomolecule or chemical, the *T. solium* polypeptides and antigenic fragments thereof described above are useful for purposes such as diagnostics and laboratory research using the methods and assays described below. Various types of labels and methods of conjugating the labels to the polypeptides are well known to those skilled in the art. Several specific labels are set forth below.

For example, the polypeptides are conjugated to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography.

Bioluminescent labels, such as derivatives of firefly luciferin, are also useful. The bioluminescent substance is covalently bound to the polypeptide by conventional methods, and the labeled polypeptide is detected when an enzyme, such as luciferase, catalyzes a reaction with ATP causing the bioluminescent molecule to emit photons of light.

Fluorogens may also be used as labels. Examples of fluorogens include fluorescein and derivatives, phycoerythrin, allo-phycocyanin, phycocyanin, rhodamine, and Texas Red. The fluorogens are generally detected using a fluorescence detector.

The polypeptides can alternatively be labeled with a chromogen to provide an enzyme or affinity label. For example, the polypeptide can be biotinylated so that it can be utilized in a biotin-avidin reaction, which may also be coupled to a label such as an enzyme or fluorogen. Alternatively, the polypeptide can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogenic or fluorogenic dioxetane derivatives of enzyme substrates can also be used. Such labels can be detected using enzyme-linked immunoassays (ELISA) or by detecting a color change with the aid of a spectrophotometer. In addition, peptides may be labeled with colloidal gold for use in immunoelectron microscopy in accordance with methods well known to those skilled in the art.

The diagnosis of an infection by *T. solium* larvae can be determined by labeling a polypeptide as described above and detecting the label in accordance with methods well known to those skilled in the art and described in more detail below.

Detection of *T. solium* Antibodies

Many techniques are known for detecting and quantifying a component such as an antibody in a mixture and/or for measuring its amount. Immunoassays, which employ polypeptides that bind specifically to antibodies of interest, are some of the better known measurement techniques. These methods permit detection (and or quantification) of circulation *T. solium* antibodies in order to indicate the presence or level of *T. solium* infection, and in some embodiments the diagnosis of a disease or condition associated with such infection. Classical methods involve reacting a sample containing the antibody with a known excess amount of polypeptide specific for the antibody, separating bound from free antibody, and determining the amount of one or the other. Often the second antibody is labeled with a reporter group to aid in the determination of the amount of bound analyte as described above. The reporter group or "label" is commonly a fluoresent or radioactive group or an enzyme.

In one embodiment, the diagnostic method uses a rapid immunochromatographic diagnostic test (card test) assay. In a further embodiment, the diagnostic method is a rapid immunochromatographic diagnostic test (card test) assay containing one or more of the larval *T. solium* glycoprotein antigens referred to herein as gp50a, -b, or -c, or antigenic fragments thereof. As mentioned above, these polypeptides have the amino acid sequences set forth in the Sequence Listing as SEQ ID NOs: 2, 4 and 6, respectively, and are encoded by the nucleic acid sequences set forth in the Sequence Listing as SEQ ID NOs: 1, 3, and 5.

It is to be understood that the assay methods are contemplated to include the use of synthetic and recombinant *T. solium* polypeptides as described above and fragments or derivatives of the *T. solium* polypeptides described herein as long as the polypeptide fragments or derivatives retain antigenic activity or display an equivalent antigenic activity of the entire immunogenic polypeptides. These fragments or derivatives include peptides with antigenic activity that have amino acid substitutions or have other molecules attached to amino acid functional groups as described above.

It is to be understood that the assay methods are contemplated to include the use of synthetic and recombinant *T. solium* polypeptides as described above, in combination with one or more other known *T. solium* polypeptides, or fragments or derivatives thereof. These other polypeptides include, but are not limited to, gp 39-42, gp24, gp21, gp18, gp14 and gp13.

An immunoassay for the detection of *T. solium* in a sample can be performed as follows: A sample is collected or obtained using methods well known to those skilled in the art. The sample containing the *T. solium* antibodies to be detected may be obtained from any biological source. Examples of biological sources include, but are not limited to, blood serum, blood plasma, urine, spinal fluid, saliva, fermentation fluid, lymph fluid, tissue culture fluid and ascites fluid of a human or animal. The sample may be diluted, purified, concentrated, filtered, dissolved, suspended, or otherwise manipulated prior to immunoassay to optimize the immunoassay results.

To detect *T. solium* antibodies in the sample, the sample is incubated with one or more *T. solium* recombinant or synthetic polypeptides, produced or obtained as described above. The polypeptide may be labeled or conjugated to a solid phase bead or particle as also described herein. The labeled polypeptide is then detected using well known techniques for detection of biologic molecules such as immunochemical or histological methods. Such methods include immunological techniques employing monoclonal or polyclonal antibodies to the polypeptide, such as enzyme linked immunosorbant assays, radioimmunoassay, chemiluminescent assays, or other types of assays involving antibodies known to those skilled in the art.

In general, binding assays rely on the binding of analyte by analyte receptors to determine the concentrations of analyte in a sample. These immunoassays can be described as either competitive or non-competitive. Non-competitive assays generally utilize analyte receptors in substantial excess over the concentration of analyte to be determined in the assay. Sandwich assays are examples of non-competitive assays, which comprise one analyte receptor frequently bound to a solid phase and a second analyte receptor labeled to permit detection. The analyte first binds to the analyte receptor bound to a solid phase and the second labeled analyte receptor is then added to facilitate quantitation of the analyte. Bound analyte can easily be separated from unbound reagents, such as unbound labeled first analyte receptors, due to the use of an analyte receptor bound to a solid phase. Competitive assays generally involve a sample suspected of containing analyte, an analyte-analogue conjugate, and the competition of these species for a limited number of binding sites provided by the analyte receptor. Competitive assays can be further described as being either homogeneous or heterogeneous. In homogeneous assays all of the reactants participating in the competition are mixed together and the quantity of analyte is determined by its effect on the extent of binding between analyte receptor and analyte-conjugate or analyte analogue-conjugate. The signal observed is modulated by the extent of this binding and can be related to the amount of analyte in the sample.

In certain embodiments, the method for detecting larval *T. solium* antibodies comprises obtaining biological samples, such as fluids and tissues, from a human or animal for the diagnosis or prognosis of cysticercosis. The sample may be obtained, for instance, from the blood, cerebrospinal fluid, urine, saliva, or tissues of a mammal, such as a human or pig. A determination of the presence of the antibodies can then be made using the recombinant or synthetic polypeptides or antigenic fragments thereof described herein as reagents in assays using assay techniques that are well known to those skilled in the art and include methods such as rapid immunochromatographic diagnostic tests, Western blot analysis, radioimmunoassay and ELISA assays.

Kits for Detecting the Presence of *T. solium*, or for Diagnosis of a *T. solium*-associated Disease or Condition Kits for detecting the presence and quantity of *T. solium* in a biological sample, or for diagnosis a *T. solium*-associated disease or condition, are also provided. The kits can be in any configuration well known to those of ordinary skill in the art and are useful for performing one or more of the assays described herein for the detection of *T. solium* in biological samples or for the detection or monitoring of *T. solium* infection in a patient or carrier. The kits are convenient in that they supply many, if not all, of the essential reagents for conducting an assay for the detection of *T. solium* in a biological sample. The reagents may be pre-measured and contained in a stable form in vessels or on a solid phase in or on which the assay may be performed, thereby minimizing the number of manipulations carried out by the individual conducting the assay. In addition, the assay may be performed simultaneously with a standard that is included with the kit, such as a predetermined amount of antigen or antibody, so that the results of the test can be validated or measured.

In certain embodiments, the kits contain one or more of the recombinant or synthetic *T. solium* polypeptides or nucleic acid molecules described herein that can be used for the detection of *T. solium* antibodies or nucleic acid molecules in a sample. The kits can additionally contain the appropriate reagents for binding the polypeptides to the antibodies or hybridizing the nucleic acid molecules to their respective *T. solium* complementary nucleic acid molecules in the sample as described herein and reagents that aid in detecting the antibody-polypeptide or nucleic acid molecule complexes. The kits may additionally contain equipment for safely obtaining the sample, a vessel for containing the reagents, a timing means, a buffer for diluting the sample, and a colorimeter, reflectometer, or standard against which a color change may be measured.

In specific embodiments, the reagents, including the polypeptides, are lyophilized, for instance in a single vessel.

Addition of aqueous sample to the vessel results in solubilization of the lyophilized reagents, causing them to react. In certain specific examples, the reagents are sequentially lyophilized in a single container, in accordance with methods that minimize reaction by the reagents prior to addition of the sample. Such methods are well known to those of ordinary skill in the art.

Specific examples of assay kits include, but are not limited to, reagents to be employed in one or more of the following techniques: competitive and non-competitive assays, radioimmunoassay, bioluminescence and chemiluminescence assays, fluorometric assays, sandwich assays, immunoradiometric assays, dot blots, enzyme linked assays including immunoblots and ELISAs, and immunocytochemistry. Materials used in conjunction with these techniques include, but are not limited to, microtiter plates, antibody coated strips or dipsticks for rapid monitoring of urine or blood. For each kit, the range, sensitivity, precision, reliability, specificity, and reproducibility of the assay are established.

In another embodiment, the assay kit uses immunoblot techniques and provides instructions and recombinant larval *T. solium* polypeptides conjugated to a detectable molecule. The kit is useful for the detection and measurement of *T. solium* in biological fluids and tissue acts of animals and humans to diagnose or monitor cysticercosis or neurocysticercosis.

Immunological and Pharmaceutical Compositions

Immunological compositions, including immunological elicitor compositions and vaccines, and other pharmaceutical compositions containing the *T. solium* polypeptides or antigenic fragments thereof described herein are useful for reducing or possibly preventing *T. solium* infection or transmission. One or more of the polypeptides described herein are formulated and packaged, alone or in combination with adjuvants or other antigens, using methods and materials known to those skilled in the vaccine art. The immunological response may be used therapeutically or prophylactically and may provide antibody immunity or cellular immunity such as that produced by T lymphocytes such as cytotoxic T lymphocytes or $CD4^+$ T lymphocytes.

To enhance immunogenicity, one or more of the polypeptides may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 Daltons, and in some embodiments greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Alternatively, a multiple antigenic polypeptide comprising multiple copies of the protein or polypeptide, or an antigenically or immunologically equivalent polypeptide may be sufficiently antigenic to improve immunogenicity without the use of a carrier.

The *T. solium* polypeptides may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. (*J. Immunol.* 147:410-415, 1991), encapsulation of the conjugate within a proteoliposome as described by Miller et al. (*J. Exp. Med.* 176:1739-1744, 1992), and encapsulation of the protein in lipid vesicles may also be useful.

The term "vaccine" as used herein includes DNA vaccines in which the nucleic acid molecule encoding *T. solium* polypeptides in a pharmaceutical composition is administered to a patient. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992) and (Eisenbraun et al., *DNA Cell Biol.* 12:791, 1993), and in vivo infection using cloned retroviai vectors (Seeger et al., *Proc. Natl. Acad. Sci.* 81:5849, 1984).

In a particular embodiment, a vaccine is packaged in a single dosage for immunization by parenteral (i.e., intramuscular, intradermal or subcutaneous) administration or nasopharyngeal (i.e., intranasal) administration. In certain embodiments, the vaccine is injected intramuscularly into the deltoid muscle. The vaccine may be combined with a pharmaceutically acceptable carrier to facilitate administration. The carrier is, for instance, water or a buffered saline, with or without a preservative. The vaccine may be lyophilized for resuspension at the time of administration or in solution.

The carrier to which the polypeptide may be conjugated may also be a polymeric delayed release system. Synthetic polymers are particularly useful in the formulation of a vaccine to effect the controlled release of antigens.

Microencapsulation of the polypeptide will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,l-lactide-co-glycolide) (PLGA) and other biodegradable polymers.

Doses for human administration of the pharmaceutical composition or vaccine may be from about 0.01 mg/kg to 10 mg/kg, for instance approximately 1 mg/kg. Based on this range, equivalent dosages for heavier body weights can be determined. The dose should be adjusted to suit the individual to whom the composition is administered, and may vary with age, weight, and metabolism of the individual. Such determinations are left to the attending physician or another familiar with the patient and/or the specific situation. The vaccine may additionally contain stabilizers or physiologically acceptable preservatives such as thimerosal(ethyl(2-mercaptobenzoate-S)mercury sodium salt) (Sigma Chemical Company, St. Louis, Mo.).

This invention is further illustrated by the following example, which is not to be construed in any way as imposing limitations upon the scope thereof. On the contrary, it will be clearly understood that resort may be had to various other embodiments, modifications, and equivalents thereof which, after reading the description herein, may suggest themselves to those of ordinary skill in the art, without departing from the spirit of the present invention and/or the scope of the appended claims.

EXAMPLE 1

Expression and Analysis of 50 kDa *T. solium* Polypeptide Chains

The coding regions for three mature gp50 polypeptides, set forth in SEQ ID NOs: 1, 3, and 5, were subcloned into the expression vector pBlueBac4.5/V5-His TOPO, a baculovirus transfer vector. Recombinant virus, containing the sequence for gp50, was formed by cotransfection of the transfer vector with Bac-N-Blue AcMNPV linear DNA, a modified baculovirus vector, in Sf9 insect cells. After purification of the recombinant virus, Sf9 cells were infected and harvested at 96 hours post-infection. Total cell lysates, from cultures infected with the recombinant virus and from cultures infected with wild type virus, were analyzed by immunoblot.

The lysates were resolved on SDS-PAGE, blotted onto nitrocellulose, and probed with cysticercosis infection sera, a serum from an Alaskan native who had an *Echinococcus multilocularis* infection, and sera from healthy humans residing in the United States with no history of travel. The anti-cysticercosis antibodies specifically recognized the gp50 recombinant proteins, which migrated in SDS-PAGE at about 31 kDa. No reactivity with recombinant GP50 was seen with the *Echinococcus* infection serum or the normal human sera. There was no reactivity seen with a band at the same position in the wild type virus infected cells.

In addition, in a second small study using 19 sera, recombinant gp50 was not recognized by all five normal or heterologous infection sera tested. The recombinant gp50 was recognized by four out of four sera that are negative with synthetic Ts14, indicating that gp50 is highly sensitive and specific, and recombinant gp50 was recognized by 10 out of 10 sera from confirmed infected cases.

We claim:

1. A composition comprising at least one synthetic larval *T. solium* polypeptide, wherein the polypeptide comprises SEQ ID NO: 2 and is immunoreactive with anti-*T. solium* larval gp50a antibodies.

2. The composition of claim 1 wherein the polypeptide is encoded by a nucleic acid molecule comprising SEQ ID NO: 1.

3. The composition of claim 1 wherein the polypeptide is a recombinant polypeptide.

4. The composition of claim 1, wherein the polypeptide is conjugated to a solid phase particle.

5. The composition of claim 1, wherein the polypeptide is conjugated to a bead.

6. The composition of claim 1, wherein the composition is lyophilized.

7. The composition of claim 1, wherein the polypeptide comprises a label.

8. An isolated polypeptide consisting of SEQ ID NO: 2.

9. The isolated polypeptide of claim 8, wherein the polypeptide is conjugated to a solid phase particle.

10. The isolated polypeptide of claim 8, wherein the polypeptide is conjugated to a bead.

11. The isolated polypeptide of claim 8, wherein the polypeptide comprises a label.

* * * * *

UNITED STATES PATENT AND TRADEMARK OFFICE
CERTIFICATE OF CORRECTION

PATENT NO. : 7,595,059 B2  Page 1 of 1
APPLICATION NO. : 11/508046
DATED : September 29, 2009
INVENTOR(S) : Tsang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 505 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 1038
<212> TYPE: DNA
<213> ORGANISM: Taenia solium
<220> FEATURE:
<221> NAME/KEY: CDS
<222> LOCATION: (3)..(875)

<400> SEQUENCE: 1

```
tc att ttt gtc gtt tct act tca agt gaa aat gcc cca aag atg tgg         47
   Ile Phe Val Val Ser Thr Ser Ser Glu Asn Ala Pro Lys Met Trp
   1               5                  10                  15 ggg tca cga gtg att gga aag cca tcg gga cct tcg gac aca atg tcc         95
Gly Ser Arg Val Ile Gly Lys Pro Ser Gly Pro Ser Asp Thr Met Ser
                20                  25                  30 tac gag tac aat gac aac tat aga acg gtt ctc atc aac gat tca gta        143
Tyr Glu Tyr Asn Asp Asn Tyr Arg Thr Val Leu Ile Asn Asp Ser Val
            35                  40                  45 ctg gga aca atg tca att aaa cgc aac caa tgc atg ctc tgg gaa aca        191
Leu Gly Thr Met Ser Ile Lys Arg Asn Gln Cys Met Leu Trp Glu Thr
        50                  55                  60 aaa cct tgg ggc gaa ccc tgt aat ata ttt cca ggt tat gtt aac ata        239
Lys Pro Trp Gly Glu Pro Cys Asn Ile Phe Pro Gly Tyr Val Asn Ile
    65                  70                  75 act ctg aat aac gtg act gca caa aag atc atg gag atg gac gag ata        287
Thr Leu Asn Asn Val Thr Ala Gln Lys Ile Met Glu Met Asp Glu Ile
80                  85                  90                  95 aca gct cgt cct aga gtg gcc tca aca acg ttc ttc gtg cca cat tgc        335
Thr Ala Arg Pro Arg Val Ala Ser Thr Thr Phe Phe Val Pro His Cys
                100                 105                 110 aat ttt aca aag cct gct cca ggt gaa gtt gat gtg tgg acg tcg ttc        383
Asn Phe Thr Lys Pro Ala Pro Gly Glu Val Asp Val Trp Thr Ser Phe
            115                 120                 125 cct ctt tcc aga ttc gtc aaa gac act cct tgg ttt aga gtc gat ttc        431
Pro Leu Ser Arg Phe Val Lys Asp Thr Pro Trp Phe Arg Val Asp Phe
        130                 135                 140 gct gtt gga ggt gca aac tac gac tct acg gcg act ttt gac atc aat        479
Ala Val Gly Gly Ala Asn Tyr Asp Ser Thr Ala Thr Phe Asp Ile Asn
```

```
gca aca tca ttg tgc ttt tgg agg gga act aaa ctt tta cac aaa gga      527
Ala Thr Ser Leu Cys Phe Trp Arg Gly Thr Lys Leu Leu His Lys Gly
160             165                 170                 175 gcc gaa ttc tgc acc gac atg gtg aaa gat gaa agc gca gat ttg agg      575
Ala Glu Phe Cys Thr Asp Met Val Lys Asp Glu Ser Ala Asp Leu Arg
                180                 185                 190 gta ttt cgt gga gtg ttc cca agg aaa act aac ata tct cgt gaa agc      623
Val Phe Arg Gly Val Phe Pro Arg Lys Thr Asn Ile Ser Arg Glu Ser
            195                 200                 205 ttt gct ttt gct ggc ctc aag act gct ctg act gtg tcc atc gac tat      671
Phe Ala Phe Ala Gly Leu Lys Thr Ala Leu Thr Val Ser Ile Asp Tyr
        210                 215                 220 tca caa agt gga ata tcg ccg gag gtg gcg gat tgc aag caa tat gcc      719
Ser Gln Ser Gly Ile Ser Pro Glu Val Ala Asp Cys Lys Gln Tyr Ala
    225                 230                 235 aaa gta aag gac ttg tca act ctg gta gcc acc atg cct gcg tac gcg      767
Lys Val Lys Asp Leu Ser Thr Leu Val Ala Thr Met Pro Ala Tyr Ala
240                 245                 250                 255 act aag act tct acc agg aac aac tca aag acg act tca tcc ggc ccc      815
Thr Lys Thr Ser Thr Arg Asn Asn Ser Lys Thr Thr Ser Ser Gly Pro
                260                 265                 270 gcg tcg atg cac acc tgc aga gca atc att gca ttg ctg tta ata cca      863
Ala Ser Met His Thr Cys Arg Ala Ile Ile Ala Leu Leu Leu Ile Pro
            275                 280                 285 atg gtt ttg tga gtgtaaccgt ttgaaggcgt ggaagcagaa atggtccaag          915
Met Val Leu
        290 gactacatta actttaacac tctgcaactt cctttgcata gttttgttct ttcctaaatg    975 tgtcttctgg ttttgcaaag taaaaataaa ctcttgttgt gttttaaaaa aaaaaaaaaa   1035 aaa                                                                 1038

<210> SEQ ID NO 2
<211> LENGTH: 290
<212> TYPE: PRT
<213> ORGANISM: Taenia solium

<400> SEQUENCE: 2

Ile Phe Val Val Ser Thr Ser Ser Glu Asn Ala Pro Lys Met Trp Gly
1               5                   10                  15

Ser Arg Val Ile Gly Lys Pro Ser Gly Pro Ser Asp Thr Met Ser Tyr
            20                  25                  30

Glu Tyr Asn Asp Asn Tyr Arg Thr Val Leu Ile Asn Asp Ser Val Leu
        35                  40                  45

Gly Thr Met Ser Ile Lys Arg Asn Gln Cys Met Leu Trp Glu Thr Lys
    50                  55                  60

Pro Trp Gly Glu Pro Cys Asn Ile Phe Pro Gly Tyr Val Asn Ile Thr
65                  70                  75                  80

Leu Asn Asn Val Thr Ala Gln Lys Ile Met Glu Met Asp Glu Ile Thr
                85                  90                  95

Ala Arg Pro Arg Val Ala Ser Thr Thr Phe Val Pro His Cys Asn
            100                 105                 110

Phe Thr Lys Pro Ala Pro Gly Glu Val Asp Val Trp Thr Ser Phe Pro
        115                 120                 125

Leu Ser Arg Phe Val Lys Asp Thr Pro Trp Phe Arg Val Asp Phe Ala
    130                 135                 140
```

```
Val Gly Gly Ala Asn Tyr Asp Ser Thr Ala Thr Phe Asp Ile Asn Ala
145                 150                 155                 160

Thr Ser Leu Cys Phe Trp Arg Gly Thr Lys Leu Leu His Lys Gly Ala
            165                 170                 175

Glu Phe Cys Thr Asp Met Val Lys Asp Glu Ser Ala Asp Leu Arg Val
        180                 185                 190

Phe Arg Gly Val Phe Pro Arg Lys Thr Asn Ile Ser Arg Glu Ser Phe
    195                 200                 205

Ala Phe Ala Gly Leu Lys Thr Ala Leu Thr Val Ser Ile Asp Tyr Ser
210                 215                 220

Gln Ser Gly Ile Ser Pro Glu Val Ala Asp Cys Lys Gln Tyr Ala Lys
225                 230                 235                 240

Val Lys Asp Leu Ser Thr Leu Val Ala Thr Met Pro Ala Tyr Ala Thr
                245                 250                 255

Lys Thr Ser Thr Arg Asn Asn Ser Lys Thr Thr Ser Ser Gly Pro Ala
            260                 265                 270

Ser Met His Thr Cys Arg Ala Ile Ile Ala Leu Leu Leu Ile Pro Met
        275                 280                 285

Val Leu
    290

<210> SEQ ID NO 3
<211> LENGTH: 1038
<212> TYPE: DNA
<213> ORGANISM: Taenia solium
<220> FEATURE:
<221> NAME/KEY: CDS
<222> LOCATION: (3)..(875)

<400> SEQUENCE: 3
```

| | | |
|---|---|---|
| tc att ttt gtc gtt tct act tca agt gaa aat gcc cca aag atg tgg<br>   Ile Phe Val Val Ser Thr Ser Ser Glu Asn Ala Pro Lys Met Trp<br>    1               5                  10                  15 | 47 |
| ggg tca cga gtg att gga aag cca tcg gga cct tcg gac aca atg tcc<br>Gly Ser Arg Val Ile Gly Lys Pro Ser Gly Pro Ser Asp Thr Met Ser<br>             20                  25                  30 | 95 |
| tac gag tac aat gac aac tat aga acg gtt ctc atc aac gat tca gta<br>Tyr Glu Tyr Asn Asp Asn Tyr Arg Thr Val Leu Ile Asn Asp Ser Val<br>         35                  40                  45 | 143 |
| ctg gga aca atg tca att aaa cgc aac caa tgc atg ctc tgg gaa aca<br>Leu Gly Thr Met Ser Ile Lys Arg Asn Gln Cys Met Leu Trp Glu Thr<br>     50                  55                  60 | 191 |
| aaa cct tgg ggc gaa ccc tgt aat ata ttt cca ggt tat gtt aac ata<br>Lys Pro Trp Gly Glu Pro Cys Asn Ile Phe Pro Gly Tyr Val Asn Ile<br> 65                  70                  75 | 239 |
| act ctg aat aac gtg act gca caa aag atc atg gag atg gac gag ata<br>Thr Leu Asn Asn Val Thr Ala Gln Lys Ile Met Glu Met Asp Glu Ile<br>80                  85                  90                  95 | 287 |
| aca gct cgt cct aga gtg gcc tca aca acg ttc ttc gtg cca cat tgc<br>Thr Ala Arg Pro Arg Val Ala Ser Thr Thr Phe Phe Val Pro His Cys<br>             100                 105                 110 | 335 |
| aat ttt aca aag cct gct cca ggt gaa gtt gat gtg tgg acg tcg ttc<br>Asn Phe Thr Lys Pro Ala Pro Gly Glu Val Asp Val Trp Thr Ser Phe<br>         115                 120                 125 | 383 |
| cct ctt tcc aga ttc gtc aaa gac act cct tgg ttt aga gtc gat ttc<br>Pro Leu Ser Arg Phe Val Lys Asp Thr Pro Trp Phe Arg Val Asp Phe<br>     130                 135                 140 | 431 |
| gct gtt gga ggt gca aac tac gac tct acg gcg act ttt gac atc aat<br>Ala Val Gly Gly Ala Asn Tyr Asp Ser Thr Ala Thr Phe Asp Ile Asn<br> 145                 150                 155                 160 | 479 |

```
                 145                 150                 155
gca aca tca ttg tgc ttt tgg agg gga act aaa ctt tta cac aaa gga      527
Ala Thr Ser Leu Cys Phe Trp Arg Gly Thr Lys Leu Leu His Lys Gly
160                 165                 170                 175 gcc gaa ttc tgc acc gac atg gtg aaa gat gaa agc gca gat ttg agg      575
Ala Glu Phe Cys Thr Asp Met Val Lys Asp Glu Ser Ala Asp Leu Arg
                180                 185                 190 gta ttt cgt gga gtg ttc cca agg aaa act aac ata tct cgt gaa agc      623
Val Phe Arg Gly Val Phe Pro Arg Lys Thr Asn Ile Ser Arg Glu Ser
            195                 200                 205 ttt gct ttt gct ggc ctc aag act gct ctg act gtg tcc atc gac tat      671
Phe Ala Phe Ala Gly Leu Lys Thr Ala Leu Thr Val Ser Ile Asp Tyr
        210                 215                 220 tca caa agt gga ata tcg ccg gag gtg gcg gat tgc aag caa tat gcc      719
Ser Gln Ser Gly Ile Ser Pro Glu Val Ala Asp Cys Lys Gln Tyr Ala
    225                 230                 235 aaa gta aag gac ttg tca act ctg gta gcc acc atg cct gcg tac gcg      767
Lys Val Lys Asp Leu Ser Thr Leu Val Ala Thr Met Pro Ala Tyr Ala
240                 245                 250                 255 act aag act tct acc ggg aac aac tca aag acg act tca tcc ggc ccc      815
Thr Lys Thr Ser Thr Gly Asn Asn Ser Lys Thr Thr Ser Ser Gly Pro
                260                 265                 270 gcg tcg aca aac gct ttc aaa gca atc att gca ttg ctg tta ata cca      863
Ala Ser Thr Asn Ala Phe Lys Ala Ile Ile Ala Leu Leu Leu Ile Pro
            275                 280                 285 atg gtt ttg tga gtgtaaccgt ttgaaggcgt ggaaacagaa atggtccaag          915
Met Val Leu
        290 gactacatta actttaacac tctgcaactt cctttgcata gttttgctct ttcctaaatg    975 tgtcttctgg ttttgcaaag taaaaataaa ctcttgttat gttttaaaaa aaaaaaaaaa   1035 aaa                                                                 1038

<210> SEQ ID NO 4
<211> LENGTH: 290
<212> TYPE: PRT
<213> ORGANISM: Taenia solium

<400> SEQUENCE: 4

Ile Phe Val Val Ser Thr Ser Ser Glu Asn Ala Pro Lys Met Trp Gly
1               5                   10                  15

Ser Arg Val Ile Gly Lys Pro Ser Gly Pro Ser Asp Thr Met Ser Tyr
            20                  25                  30

Glu Tyr Asn Asp Asn Tyr Arg Thr Val Leu Ile Asn Asp Ser Val Leu
        35                  40                  45

Gly Thr Met Ser Ile Lys Arg Asn Gln Cys Met Leu Trp Glu Thr Lys
    50                  55                  60

Pro Trp Gly Glu Pro Cys Asn Ile Phe Pro Gly Tyr Val Asn Ile Thr
65                  70                  75                  80

Leu Asn Asn Val Thr Ala Gln Lys Ile Met Glu Met Asp Glu Ile Thr
                85                  90                  95

Ala Arg Pro Arg Val Ala Ser Thr Thr Phe Phe Val Pro His Cys Asn
            100                 105                 110

Phe Thr Lys Pro Ala Pro Gly Glu Val Asp Val Trp Thr Ser Phe Pro
        115                 120                 125

Leu Ser Arg Phe Val Lys Asp Thr Pro Trp Phe Arg Val Asp Phe Ala
    130                 135                 140
```

```
Val Gly Gly Ala Asn Tyr Asp Ser Thr Ala Thr Phe Asp Ile Asn Ala
145                 150                 155                 160

Thr Ser Leu Cys Phe Trp Arg Gly Thr Lys Leu Leu His Lys Gly Ala
            165                 170                 175

Glu Phe Cys Thr Asp Met Val Lys Asp Glu Ser Ala Asp Leu Arg Val
        180                 185                 190

Phe Arg Gly Val Phe Pro Arg Lys Thr Asn Ile Ser Arg Glu Ser Phe
    195                 200                 205

Ala Phe Ala Gly Leu Lys Thr Ala Leu Thr Val Ser Ile Asp Tyr Ser
210                 215                 220

Gln Ser Gly Ile Ser Pro Glu Val Ala Asp Cys Lys Gln Tyr Ala Lys
225                 230                 235                 240

Val Lys Asp Leu Ser Thr Leu Val Ala Thr Met Pro Ala Tyr Ala Thr
                245                 250                 255

Lys Thr Ser Thr Gly Asn Asn Ser Lys Thr Thr Ser Ser Gly Pro Ala
            260                 265                 270

Ser Thr Asn Ala Phe Lys Ala Ile Ile Ala Leu Leu Leu Ile Pro Met
        275                 280                 285

Val Leu
    290

<210> SEQ ID NO 5
<211> LENGTH: 1016
<212> TYPE: DNA
<213> ORGANISM: Taenia solium
<220> FEATURE:
<221> NAME/KEY: CDS
<222> LOCATION: (1)..(849)

<400> SEQUENCE: 5 agt gaa aat gcc cca aag atg tgg ggg tca cga gtg att gga aag cca      48
Ser Glu Asn Ala Pro Lys Met Trp Gly Ser Arg Val Ile Gly Lys Pro
1               5                   10                  15 tcg gga cct tcg gac aca atg tcc tac gag tac aat gac aac tat aga     96
Ser Gly Pro Ser Asp Thr Met Ser Tyr Glu Tyr Asn Asp Asn Tyr Arg
            20                  25                  30 acg gtt ctc atc aac gat tca gta ctg gga aca atg tca att aaa cgc    144
Thr Val Leu Ile Asn Asp Ser Val Leu Gly Thr Met Ser Ile Lys Arg
        35                  40                  45 aac caa tgc atg ctc tgg gaa aca aaa cct tgg ggc gaa ccc tgt aat    192
Asn Gln Cys Met Leu Trp Glu Thr Lys Pro Trp Gly Glu Pro Cys Asn
    50                  55                  60 ata ttt cca ggt tat gtt aac ata act ctg aat aac gtg act gca caa    240
Ile Phe Pro Gly Tyr Val Asn Ile Thr Leu Asn Asn Val Thr Ala Gln
65                  70                  75                  80 aag atc atg gag atg gac gag ata aca gct cgt cct aga gtg gcc tca    288
Lys Ile Met Glu Met Asp Glu Ile Thr Ala Arg Pro Arg Val Ala Ser
                85                  90                  95 aca acg ttc ttc gtg cca cat tgc aat ttt aca aag cct gct cca ggt    336
Thr Thr Phe Phe Val Pro His Cys Asn Phe Thr Lys Pro Ala Pro Gly
            100                 105                 110 gaa gtt gat gtg tgg acg tcg ttc cct ctt tcc aga ttc gtc aaa gac    384
Glu Val Asp Val Trp Thr Ser Phe Pro Leu Ser Arg Phe Val Lys Asp
        115                 120                 125 act cct tgg ttt aga gtc gat ttc gct gtt gga ggt gca aac tac gac    432
Thr Pro Trp Phe Arg Val Asp Phe Ala Val Gly Gly Ala Asn Tyr Asp
    130                 135                 140 tct acg gcg act ttt gac atc aat gca aca tca ttg tgc ttt tgg agg    480
Ser Thr Ala Thr Phe Asp Ile Asn Ala Thr Ser Leu Cys Phe Trp Arg
145                 150                 155                 160
```

-continued

```
                145                 150                 155                 160
gga act aaa ctt tta cac aaa gga gcc gaa ttc tgc acc gac atg gtg        528
Gly Thr Lys Leu Leu His Lys Gly Ala Glu Phe Cys Thr Asp Met Val
                165                 170                 175 aaa gat gaa agc gca gat ttg agg gta ttt cgt gga gtg ttc cca agg        576
Lys Asp Glu Ser Ala Asp Leu Arg Val Phe Arg Gly Val Phe Pro Arg
            180                 185                 190 aaa act aac ata tct cgt gaa agc ttt gct ttt gct ggc ctc aag act        624
Lys Thr Asn Ile Ser Arg Glu Ser Phe Ala Phe Ala Gly Leu Lys Thr
        195                 200                 205 gct ctg act gtg tcc atc gac tat tca caa agt gga ata tcg ccg gag        672
Ala Leu Thr Val Ser Ile Asp Tyr Ser Gln Ser Gly Ile Ser Pro Glu
    210                 215                 220 gtg gcg gat tgc aag caa tat gcc aaa gta aag gac ttg tca act ctg        720
Val Ala Asp Cys Lys Gln Tyr Ala Lys Val Lys Asp Leu Ser Thr Leu
225                 230                 235                 240 gta gcc acc atg cct gcg tac gcg act aag act tct acc ggg aac aac        768
Val Ala Thr Met Pro Ala Tyr Ala Thr Lys Thr Ser Thr Gly Asn Asn
                245                 250                 255 tca aag acg act tca tcc ggc ccc gcg tcg atg cac acc tgc aga gca        816
Ser Lys Thr Thr Ser Ser Gly Pro Ala Ser Met His Thr Cys Arg Ala
            260                 265                 270 atc att gca ttg ctg ttg ata cca atg gtt ttg tgagtgtaac cgtttgaagg      869
Ile Ile Ala Leu Leu Leu Ile Pro Met Val Leu
        275                 280 cgtggaagca gaaatggtcc aaggactaca ttaactttaa cactctgcaa cttcctttgc      929
atagttttgt tctttcctaa atgtgtcttc tggttttgca aagtaaaaat aaactcttgt      989
tgtgttttaa aaaaaaaaaa aaaaaaa                                         1016
```

<210> SEQ ID NO 6
<211> LENGTH: 283
<212> TYPE: PRT
<213> ORGANISM: Taenia solium

<400> SEQUENCE: 6

```
Ser Glu Asn Ala Pro Lys Met Trp Gly Ser Arg Val Ile Gly Lys Pro
1               5                   10                  15

Ser Gly Pro Ser Asp Thr Met Ser Tyr Glu Tyr Asn Asp Asn Tyr Arg
            20                  25                  30

Thr Val Leu Ile Asn Asp Ser Val Leu Gly Thr Met Ser Ile Lys Arg
        35                  40                  45

Asn Gln Cys Met Leu Trp Glu Thr Lys Pro Trp Gly Glu Pro Cys Asn
    50                  55                  60

Ile Phe Pro Gly Tyr Val Asn Ile Thr Leu Asn Asn Val Thr Ala Gln
65                  70                  75                  80

Lys Ile Met Glu Met Asp Glu Ile Thr Ala Arg Pro Arg Val Ala Ser
                85                  90                  95

Thr Thr Phe Phe Val Pro His Cys Asn Phe Thr Lys Pro Ala Pro Gly
            100                 105                 110

Glu Val Asp Val Trp Thr Ser Phe Pro Leu Ser Arg Phe Val Lys Asp
        115                 120                 125

Thr Pro Trp Phe Arg Val Asp Phe Ala Val Gly Gly Ala Asn Tyr Asp
    130                 135                 140

Ser Thr Ala Thr Phe Asp Ile Asn Ala Thr Ser Leu Cys Phe Trp Arg
145                 150                 155                 160

Gly Thr Lys Leu Leu His Lys Gly Ala Glu Phe Cys Thr Asp Met Val
```

-continued

```
                165                 170                 175
Lys Asp Glu Ser Ala Asp Leu Arg Val Phe Arg Gly Val Phe Pro Arg
            180                 185                 190

Lys Thr Asn Ile Ser Arg Glu Ser Phe Ala Phe Ala Gly Leu Lys Thr
            195                 200                 205

Ala Leu Thr Val Ser Ile Asp Tyr Ser Gln Ser Gly Ile Ser Pro Glu
        210                 215                 220

Val Ala Asp Cys Lys Gln Tyr Ala Lys Val Lys Asp Leu Ser Thr Leu
225                 230                 235                 240

Val Ala Thr Met Pro Ala Tyr Ala Thr Lys Thr Ser Thr Gly Asn Asn
            245                 250                 255

Ser Lys Thr Thr Ser Ser Gly Pro Ala Ser Met His Thr Cys Arg Ala
            260                 265                 270

Ile Ile Ala Leu Leu Leu Ile Pro Met Val Leu
            275                 280
```